United States Patent [19]

Silvestrini

[11] Patent Number: 4,979,956
[45] Date of Patent: Dec. 25, 1990

[54] DEVICE AND METHOD FOR TENDON AND LIGAMENT REPAIR

[75] Inventor: Thomas A. Silvestrini, East Lyme, Conn.

[73] Assignee: Pfizer Hospital Products Group, Inc., New York, N.Y.

[21] Appl. No.: 378,437

[22] Filed: Jul. 10, 1989

Related U.S. Application Data

[63] Continuation of Ser. No. 115,087, Oct. 30, 1987, abandoned.

[51] Int. Cl.$^5$ ............................................... A61F 2/06
[52] U.S. Cl. .................................................... 623/13
[58] Field of Search .................... 623/11, 12, 16, 13, 623/18

[56] References Cited

U.S. PATENT DOCUMENTS

| | | | |
|---|---|---|---|
| 3,124,136 | 3/1964 | Usher | 623/11 |
| 3,176,316 | 4/1965 | Bodell | 3/1 |
| 3,545,008 | 12/1970 | Bader, Jr. | 623/13 |
| 3,646,615 | 3/1972 | Ness | 623/13 |
| 3,805,300 | 4/1974 | Tascon-Alonso | 623/13 |
| 3,987,497 | 10/1976 | Stoy et al. | 623/13 |
| 3,992,725 | 11/1976 | Homsy | 623/16 |
| 4,469,101 | 9/1984 | Coleman et al. | 128/334 R |
| 4,501,029 | 2/1985 | McMinn | 3/1 |
| 4,512,038 | 4/1985 | Alexander et al. | 623/13 |
| 4,585,458 | 4/1986 | Kurland | 623/13 |
| 4,610,688 | 9/1986 | Silvestrini et al. | 623/1 |

FOREIGN PATENT DOCUMENTS

| | | | |
|---|---|---|---|
| 197703 | 1/1976 | U.S.S.R. | 623/16 |
| 197708 | 8/1977 | U.S.S.R. | 128/334 R |

OTHER PUBLICATIONS

K. Cieslik et al., Early Mechanical Strength of Digital Flexor Tendon Sutures, Handchirurgie, vol. 18, Nov. 1986, pp. 347-350.

Primary Examiner—David J. Isabella
Attorney, Agent, or Firm—Peter C. Richardson; Lawrence C. Akers; John L. LaPierre

[57] ABSTRACT

A device, suitable for use in repairing a lacerated or severed tendon, particularly a hand flexor tendon, having a flat band body with opposite ends of the body designed to anchor connecting sutures. The device also finds applicability in the repair of lacerated or severed ligaments. Also disclosed is a method of repairing a severed tendon by implanting a flat band device suturing together the device and the tendon to effect an anastomosis along approximated ends of the severed tendon. Further disclosed is a method of repairing a lacerated or severed ligament.

28 Claims, 2 Drawing Sheets

DEVICE AND METHOD FOR TENDON AND LIGAMENT REPAIR

This is a continuation, of application Ser. No. 115,087, filed on Oct. 30, 1987, now abandoned.

BACKGROUND OF THE INVENTION

The present invention relates to a device for repairing severed or lacerated tendons and ligaments and, more particularly, the invention relates to a device having a flat band body constructed of resilient synthetic textile fiber and capable of receiving a suture element secured thereto at opposite ends of the body. Also contemplated by the invention are methods of anastomosing ends of severed or lacerated tendons and ligaments along an interface of approximated ends, by placing a device intratendonously, in the case of a tendon, or in juxtaposition, in the case of a ligament, bridging or spanning approximated ends, and suturing together either the tendon and the device or the ligament and the device. The objective is to provide a device and method for restoring tendons and ligaments, as nearly as possible, to their pre-damaged condition.

The successful repair of tendons, particularly hand flexor tendons, has been a problem for surgeons for many years. The past and current approach most commonly used by surgeons to achieve tendon repair is to anastomose severed tendons by using one of a variety of suturing techniques. A number of such techniques are commonly known and referred to as Bunnell, Kessler, Klienert, Tsuge and Becker, to name but a few. These techniques, while useful, are not entirely satisfactory because they allow surgeons to achieve successful repairs in only about 70% of the patients treated. Therefore, in view of the history of suture techniques which have been proposed and implemented from time to time by surgeons without any real improvement in repair strength or surgical result, the need for an improved device and method of anastomosis were clearly evident.

In addition to the foregoing suturing techniques most often used in tendon repair, in an effort to overcome the deficiencies encountered in the straight suturing approach, other devices and approaches have recently been tried to effect tendon repair. A typical device encountered might be one like that disclosed in U.S. Pat. No. 4,469,101. The teaching embodied in this patent specifies a structure having an open network or mesh of helically formed members to define a hollow tubular device wherein opposing ends of a lacerated tendon are introduced and brought into contact within the tube. The opposite ends of the tube are then sutured to the outer tendon wall and the contacting tendon ends are allowed to heal. Another device typically encountered in tendon repair might be one like that disclosed in U.S. Pat No. 4,501,029. This patent provides a continuous solid wall tubular device having in communication therewith a number of transversely extending passages. The tube is inserted between a replacement tendon and the tendon sheath. After blood supply from the sheath to the replacement tendon is established through the tubular passages, free movement of the tendon is established within the sheath. A third device encountered might be the plastic prosthetic tendon disclosed in U.S. Pat. No. 3,176,316. This patent provides a prosthesis having a solid central segment and hollow tubular ends comprising a mesh network wherein ends of a tendon are introduced and the prosthesis is sutured to the tendon.

There are certain disadvantages associated with each of the aforementioned tendon repair techniques and devices which the present inventive device and method either overcome or substantially lessen. Specifically, through the use of suturing techniques alone, irritations are minimized since sutures are buried inside the endotendon, but the strength of the anastomosis is not strong enough to allow aggressive mobility during healing. Consequently, there often occurs dehiscence of the suture leading to separation of approximated tendon ends, tissue ingrowth and slow or incomplete tendon healing. Inherent in the tubular mesh devices which are sutured to the tendon at ends of the devices is the exposure of a large amount of synthetic material on the outside of the epitenon which can cause excessive irritations. These irritations frequenty lead to adhesions between the injured tendon and the tendon surrounding which leads to retarded healing. The inventive device offers a minimum of irritation since it is substantially buried inside the endotendon, yet it offers higher strength of the anastomosed tendon compared to repairs using sutures. Lastly, the present device is one of structural simplicity which avoids both the complex geometry presented in the solid wall tubular device having a series of selectively positioned blood conveying passageways and the need to precisely locate such a prosthesis in the body to assure an adequate blood supply to the replacement tendon.

It should be understood that, while much of the foregoing discussion is directed toward tendon repair, the teachings encountered are also generally applicable to the repair of damaged ligaments. Clearly, there exists a need for a repair device which fosters superior mechanical repair properties and better healing characteristics than is currently found in the relevant surgical field. The present inventive device and method satisfies the need and, hence, advances the art field of tendon and ligament repair.

SUMMARY OF THE INVENTION

The present invention relates to a device used for repairing severed connective tissue of tendons and ligaments by approximating ends of the severed tissue and comprises an elongated body portion having a flat band structure with the body portion at opposite ends adapted to be connected to at least one needle bearing suture. The body structure may be a non-woven fabric, a composite reinforced with chopped fiber, a polymer sheet or a fabric which can be selected from a class of warp knits, weaves, nets and braids. The preferred braided fabric would be a triaxial braid or a flat band triaxial tube having either a monocomponent or bicomponent fiber element selected from a polymeric grouping and may include an elastomeric component. The preferred polymer for a monocomponent device body would be polyethylene terepthalate while for a bicomponent device the preferred polymers for the device body would be polyethylene terepthalate and polyester/polyether block copolymer. A suture or sutures may be lock stitched to opposite ends of the device body and may be incorporated into the body structure axially in either a longitudinal direction or in a bias direction. Additionally, a suture or sutures may be sewn into the body. The device body and associated suture or sutures may be covered with one or more gel coatings selected from a class of hydrogels with a preferred coating being crosslinked calcium alginate. The body portion may assume a number of shapes but either a rectangle or a polygon, having ends tapered substantially to a point, is preferred. The ends of the body portion are preferably sealed to maintain edge integrity.

Also contemplated within the scope of the present invention are methods for repairing severed connective tissue of tendons and ligaments utilizing the inventive device heretofore described. Specifically, one method comprises the steps of creating a slot in the tissue of each opposing end of a severed tendon, where severance occured, inserting a first end of the device into one of the incised slots, inserting a second end of the device into the other of the incised slots, approximating opposing ends of the severed tissue, enclosing the device and therewithin bridging the ends, and suturing the tendon and the device together, passing sutures through the tendon and the implanted device along at least a portion of the length of the device, to anastomose the tendon along approximated ends of the severed connective tissue. A second method, relating to the repair of severed connective tissue of a ligament, comprises the steps of providing at least one inventive device, approximating opposing ends of the severed tissue, juxtaposing the ligament and the device with the device spanning approximated ends, and suturing the ligament and the device together, passing sutures through the ligament and the juxtaposed device along at least a portion of the length of the device, to anastomose the ligament along approximated ends of the severed connective tissue. In each of the methods, suturing will span at least the approximated ends and, preferably, suturing will be performed along substantially the entire length of the device.

The various features of novelty which characterize the invention are pointed out with particularity in the claims annexed to and forming a part of this disclosure. For a better understanding of the invention, its operating advantages and specific results obtained by its use, reference should be made to the corresponding drawings and descriptive matter in which there is illustrated and described typical embodiments of the invention.

DETAILED DESCRIPTION OF THE PREFERRED EMBODIMENTS

Figure 1:
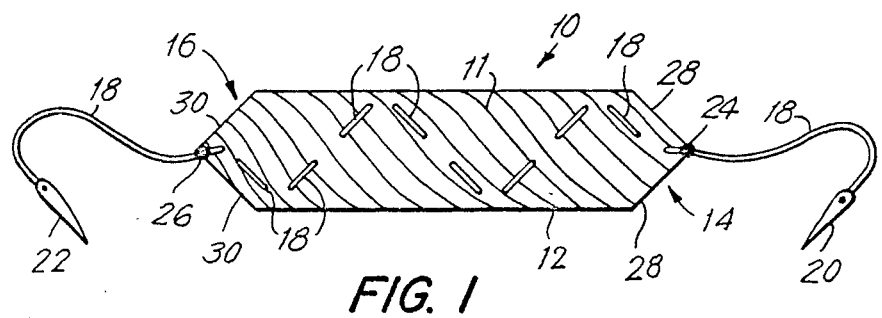
FIG. 1 is an enlarged schematic representation of a tendon and ligament repair device, in accordance with the principles of the present invention, illustrating a flat band triaxial braid fabric structure having a single bias suture incorporated into the fabric body with the suture lock stitched to the body at opposite ends of the body.

The description herein presented refers to the accompanying drawings in which like reference numerals refer to like parts throughout the several views, and in which, referring to FIG. 1, there is illustrated a repair device 10 of the present invention. The device has an elongated body portion 12 of flat band structural configuration, preferably a triaxial braid with the braid schematically designated as 11, and at a first end 14 and at a second end 16 a suture 18, having needles 20 and 22 at opposite ends, is connected or anchored to the body ends by a locking stitches 24 and 26. It should be understood that many types of knots or locking stitches, such as a double throw suture locking stitch, would be suitable to anchor the suture to the body portion. Locking the suture to the body could be accomplished at any time, as desired. The device shown in FIG. 1, it should be remembered, is a schematic representation and, therein depicted, the device has a flat band triaxial braid fabric structure with a single bias suture braided into the fabric body. It should also be understood that more than one suture could be attached to or incorporated into the fabric body and locked to the body ends. Furthermore, a suture or sutures could be sewn or stitched to the body along the body length instead of being braided into the body. In the preferred form of the device, the lock stitching of the suture to the ends of the braid body prevents the braid structure from bunching during insertion into tissue. The stitching also serves to center the suture pull of the device, thereby easing the insertion of the device into connective tissue. Also contemplated within the scope of the invention is a suture or sutures not incorporated into the fabric body per se but merely locked to one or both of the body ends. The ends 14 and 16 may be sealed along edges 28 and 30 to maintain edge integrity. Edge sealing may be accomplished using an ultrasonic sealing process or other means of heat treatment to keep edges from unraveling or separating.

The device body portion may be structurally configured as a non-woven fabric, a polymer reinforced with chopped fiber, a polymer sheet, a warp knit, a weave, a net or a braid. The construction of the desired flat band fabric into any one of these body portion structural configurations would be within the skill of those who manufacture textile products. A preferred structure would be a braid, preferably a triaxial braid. A flat band or flattened triaxial tube is within the scope of the invention. A triaxially-braided fabric, such as the ones schematically depicted in FIG. 1 and FIG. 6, and the methods of manufacturing them in different configurations, namely, flat bands, flat tubes, tubes, patches and strips, to name but a few, are well known to those skilled in the art of manufacturing braided polymeric articles. The triaxial braid may consist of a monocomponent fiber selected from a group of polymers consisting of polyethylene terepthalate, polyethylene, polypropylene, polyaramid, polyamide, polyetheretherketone, polyester/polyether block copolymer, liquid crystal polymeric fiber, nylon and carbon. The preferred polymer would be polyethylene terepthalate. The triaxial braid may also have a bicomponent fiber makeup with its components selected from the same polymer grouping. One of the components of the bicomponent braid should be elastomeric with the preferred elastomer being polyester/polyether block copolymer. The preferred bicomponent braid comprises a first component of polyethylene terepthalate and a second component of polyester/polyether block copolymer.

The device may be coated to improve the ease of surgical installation and to minimize irritation to tissue during healing. The suture or sutures could also be coated to minimize adhesions formed during healing. The coating could be a gel, specifically a hydrogel, selected from the group consisting of sodium alginate, hyaluronic acid, crosslinked hyaluronic acid, crosslinked calcium alginate and a calcium alginate crosslinked hyaluronic acid mixture. The preferred lubricious coating for the device and sutures is crosslinked calcium alginate.

Figure 6:
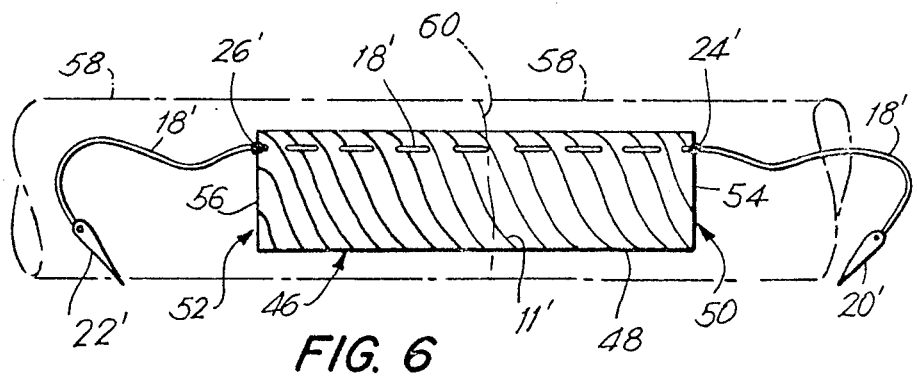
FIG. 6 is an enlarged schematic alternate embodiment of the invention showing in phantom a ligament with approximated ends and a flat band triaxial braid fabric structure, in place but prior to suturing, with a single axial suture incorporated into the fabric body with the suture lock stitched to the body at opposite ends thereof.

The device body as shown in FIG. 1 defines a polygon having opposed longitudinal ends each tapering to a point with the points, preferably, lying along the central longitudinal axis. The body may, however, as is shown in FIG. 6, take a rectangular shape. Other flat band structural shapes would be suitable and are within the scope of the present invention.

Figure 2:
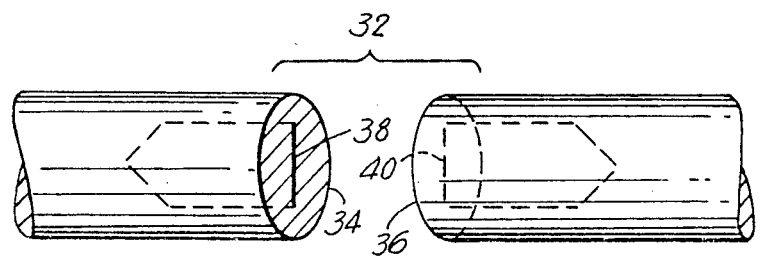
FIG. 2 schematically illustrates a severed tendon, drawn at reduced scale, with slots incised in the tendon ends, before implantation of the repair device.
Figure 3:
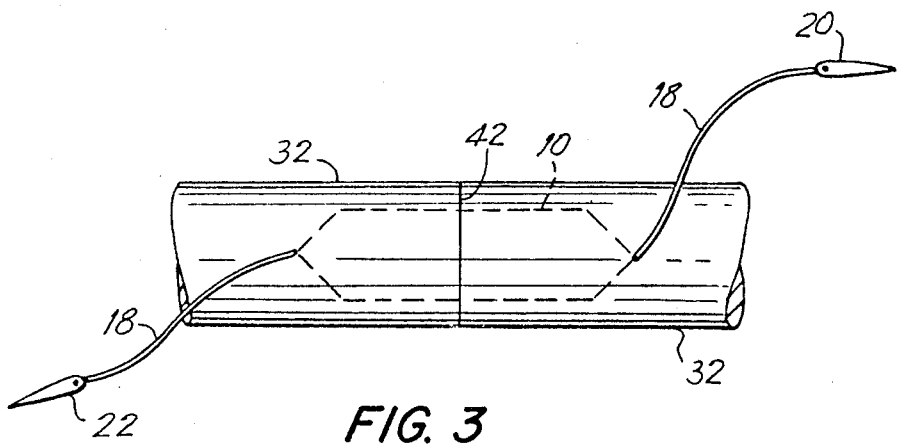
FIG. 3 is similar to FIG. 2, but with tendon ends approximated, and schematically illustrates the tendon repair device of FIG. 1 located within the endotendon prior to suturing.
Figure 4:
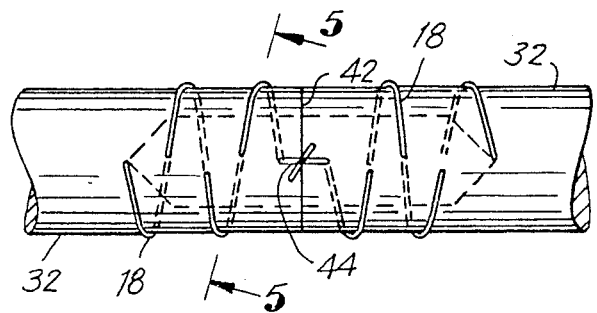
FIG. 4 is similar to FIG. 3 and illustrates a completed repair showing suture penetration of both tendon and fabric body uniting tendon and device.
Figure 5:
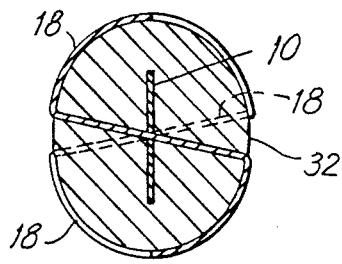
FIG. 5 is a cross-sectional view taken along line 5—5 of FIG. 4.

Turning to FIG. 2 through FIG. 5, in FIG. 2 there is shown severed connective tissue of a tendon 32 having separated ends 34 and 36. In each end 34 and 36, slots 38 and 40 have been incised within the endotendon using a suitable blade or cutting device (not shown). Each slot 38 and 40 will preferably be configured to conform substantially to one half the size of the repair device 10. FIG. 3 shows device 10 located within slots 38 and 40, suture 18 at opposite ends 14 and 16 of device 10 passing through tendon 32, and separated tissue ends 34 and 36 approximated as shown at 42. Device 10 is closed within the approximated tissue, bridging ends 34 and 36 which are in contact along joint 42. FIG. 4 and FIG. 5 depict a completed repair wherein the tendon and the device have been sutured together and the suture ends tied at 44. Suturing of the device into the tendon can be accomplished in many different ways. Thus, the device does not restrict the personal suturing preference of different surgeons. Anastomosis of the tendon will occur along approximated ends at 42. Suturing should span at least the approximated ends and, preferably suturing should be performed along substantially the entire length of the implanted device 10.

Turning to FIG. 6, there is schematically shown an alternate embodiment of the invention. Here depicted is a rectangular flat band repair device 46 having a triaxially braided fabric structure 11' and a suture 18', bearing needles 20' and 22', incorporated into elongated body portion 48 and axially oriented in a longitudinal direction. At first and second ends 50 and 52, suture 18' is affixed to the body ends by locking stitches 24' and 26'. As aforementioned in respect to the device 10, many types of knots or locking stitches would be suitable to affix the suture to the body portion and stitching could be accomplished when desired, namely, at time of manufacture or by a surgeon prior to device use. Lock stitching would be particularly useful, in addition to ease in installation, that is, prevention of fabric bunching, to keep the suture from being pulled through the fabric. More than one suture could be used and attached to or incorporated into the body fabric. Additionally, a suture might be sewn to the body along the length of the body rather than being braided into the body. The ends 50 and 52 may be sealed along edges 54 and 56 to maintain edge integrity, as in the case of device 10. All of the other structural features associated with device 10 are equally suitable for device 46.

In FIG. 6, device 46 is shown to be particularly useful in the repair of severed connective tissue of a ligament, illustrated in phantom and designated as 58. It should be understood, however, that a device of rectangular configuration would be equally useful in tendon repair and slots 38 and 40, as shown in FIG. 2, could assume a rectangular shape. Likewise, device 10 would be equally suitable in the repair of a ligament. Device 46, as provided in FIG. 6, is shown positioned alongside ligament 58 having severed ends approximated at 60. The device spans the approximated ends. It should be understood that more than one device could be used for the repair. While a completed repair is not shown in FIG. 6, a suturing technique like that shown in FIG. 4, and other techniques described in respect thereto, could be used to suture together ligament 58 and device 46. Anastomosis of the ligament will occur along approximated tissue ends at 60. Suturing should span at least the approximated ends and, preferably, suturing should be performed along substantially the entire length of device 46. In each of the repair techniques, namely, tendon and ligament, devices 10 and 46 are biocompatible and can be made from permanent, non-body absorbable materials, or from resorbable materials.

As heretofore mentioned, braiding can be accomplished using known technology and the inventive device can be manufactured using existing braiding machines modified to incorporate longitudinal fibers into the braided structures. By way of example, and not to be construed as limiting the invention, a 0.07 inch wide monocomponent polyethylene terepthalate device 10 can be braided on a 32-carrier triaxial braider using 70 denier white polyethylene terepthalate type 52 multifilament yarns and a single green 4-0 polyethylene terepthalate suture. The finished product is composed of 31 polyethylene terepthalate yarns and one 4-0 polyethylene terepthalate suture on the bias and 16 polyethylene terepthalate yarns on the longitudinal axis. In another example, a 0.07 inch wide bicomponent device 10 can be braided on a 24-carrier triaxial braider using 220 denier polyester/polyether block copolymer monofilaments, 70 denier white polyethylene terepthalate type 52 multifilament yarns, and a single green 4-0 polyethylene terepthalate suture. The finished construction is composed of 23 polyethylene terepthalate yarns and one 4-0 polyethylene terepthalate suture on the bias, and 12 polyester/polyether block copolymer fibers on the longitudinal axis. It should be understood that wider or narrower devices could be manufactured. The device is made from safe materials that surgeons are comfortable implanting and the device can easily be made in a variety of sizes to address different soft tissue repair situations. Device needles could be swaged onto the suture ends of affixed by other suitable means. Laboratory testing of a repair device used to anastomose explanted canine and bovine tendon has demonstrated that the initial strength of the repair junction is approximately twice the strength of tendon repairs made using conventional suturing techniques.

While in accordance with provisions of the statutes there is described herein specific embodiments of the invention, those skilled in the art will understand that changes may be made in the form of the invention covered by the claims appended hereto without departing from the scope and spirit thereof, and that certain features of the invention may sometimes be used to an advantage without corresponding use of the other features.

I claim:

1. A device for use in repairing severed connective tissue of tendons and ligaments by approximating severed ends of said tissue bringing said tissue ends into abutment comprising an elongated body having a flat band structure, said body being sized and configured for enclosure within said abutting tissue ends, and with said body at first and second opposed non-bifurcated ends adapted to be connected to at least one needle bearing suture, with said suture being incorporated into said body substantially the length thereof, said suture being oriented in a bias direction.

2. The device according to claim 1 wherein said structure is a non-woven fabric.

3. The device according to claim 1 wherein said structure is a polymer reinforced with chopped fiber.

4. The device according to claim 1 wherein said structure is a polymer sheet.

5. The device according to claim 1 wherein said structure is a fabric selected from the group consisting of warp knits, weaves, nets and braids.

6. The device according to claim 5 wherein said fabric is a braid.

7. The device according to claim 6 wherein said braid is a triaxial braid.

8. The device according to claim 7, wherein said braid comprises a monocomponent fiber forming element.

9. The device according to claim 8 wherein said element is a polymer selected from the group consisting of polyethylene terepthalate, polyethylene, polypropylene, polyaramid, polyamide, polyetherether ketone, polyester/polyether block copolymer, liquid crystal polymeric fibers, nylon and carbon.

10. The device according to claim 9 wherein said polymer is preferably polyethylene terepthalate.

11. The device according to claim 7 wherein said braid comprises a bicomponent fiber forming element.

12. The device according to claim 11 wherein said element is a plurality of polymers selected from the group consisting of polyethylene terepthalate, polyethylene, polypropylene, polyaramid, polyamide, polyetherether ketone, polyester/polyether block copolymer, liquid crystal polymeric fibers, nylon and carbon.

13. The device according to claim 12 wherein at least one of said polymers is elastomeric.

14. The device according to claim 13 wherein said elastomeric polymer is preferably polyester/polyether block copolymer.

15. The device according to claim 12 wherein said polymers are preferably polyethylene terepthalate and polyester/polyether block copolymer.

16. The device according to claim 1 wherein said suture is lock stitched to said ends.

17. The device according to claim 1 wherein said suture is sewn into said body.

18. The device according to claim 17 wherein said suture is axially oriented in a longitudinal direction.

19. The device according to claim 1 wherein said body is covered with a gel coating.

20. The device according to claim 19 wherein said body and said suture are covered with a gel coating.

21. The device according to claim 20 wherein said coating is a hydrogel selected from the group consisting of sodium alginate, hyaluronic acid, crosslinked hyaluronic acid, crosslinked calcium alginate and a calcium alginate crosslinked hyaluronic acid mixture.

22. The device according to claim 21 wherein said hydrogel is preferably crosslinked calcium alginate.

23. The device according to claim 1 wherein said body defines a polygon.

24. The device according to claim 23 wherein said polygon is a rectangle.

25. The device according to claim 23 wherein at least one of said ends of said body terminates substantially in a point.

26. The device according to claim 25 wherein said point lies along a central axis of said body.

27. The device according to claim 1 wherein said ends are sealed proximate end edges to maintain edge integrity.

28. The device according to claim 1 wherein said body is a flat band triaxial tube.

* * * * *